United States Patent
O'Lenick, Jr. et al.

(10) Patent No.: US 6,683,032 B1
(45) Date of Patent: Jan. 27, 2004

(54) MULTIFUNCTIONAL PHOSPHOLIPID SURFACTANTS

(76) Inventors: Anthony J. O'Lenick, Jr., 2170 Luke Edwards Rd., Dacula, GA (US) 30019; Kevin A. O'Lenick, 2170 Luke Edwards Rd., Dacula, GA (US) 30019

( * ) Notice: Subject to any disclaimer, the term of this patent is extended or adjusted under 35 U.S.C. 154(b) by 79 days.

(21) Appl. No.: 10/138,876

(22) Filed: May 6, 2002

(51) Int. Cl.$^7$ ............................................. A61K 7/075

(52) U.S. Cl. ...................... 510/122; 510/123; 554/80

(58) Field of Search ............................................ 554/80

(56) References Cited

U.S. PATENT DOCUMENTS 4,233,192 A    11/1980    Lindemann

*Primary Examiner*—Deborah D. Carr

(57) ABSTRACT

The present invention relates to novel compositions and, more particularly, to a class of compounds having specific quaternized amine based upon a phosphate ester. The use of a phosphate ester based upon a fatty alcohol or fatty alcohol alkoxylate as the material used to prepare a phospholipid results in heretofore-unknown compounds. The products are very good wetting agents, have improved hydrolytic stability, are extremely substantitive to human skin and are well tolerated by human tissue making them suitable for use preparation of barrier products for personal care applications. In short they are ideal surfactants for use in many personal care applications.

20 Claims, No Drawings

MULTIFUNCTIONAL PHOSPHOLIPID SURFACTANTS

FIELD OF THE INVENTION

The present invention relates to novel compositions and, more particularly, to a class of compounds having specific quaternized amine based upon a phosphate ester. The use of a phosphate ester based upon a fatty alcohol or fatty alcohol alkoxylate as the material used to prepare a phospholipid results in heretofore-unknown compounds. The products are very good wetting agents, have improved hydrolytic stability, are extremely substantitive to human skin and are well tolerated by human tissue making them suitable for use preparation of barrier products for personal care applications. In short they are ideal surfactants for use in many personal care applications.

BACKGROUND OF THE INVENTION

Phosphate ester and quaternary amine compounds are well known and have been widely used for many years More recently, various betaine-type derivatives having, in general, quaternized alkyl amine groups and at least one phosphorous-containing anion in the molecule referred to hereinafter as "synthetic phospholipids", have been disclosed The in U.S. Pat. Nos. are U.S. Pat. Nos. 3,856,893 and 3,928,509 to Diery et al. Diery discloses that the phosphonate compounds of his invention are active antimicrobial compounds. Later amido amine and imidazoline derivatives were disclosed for example, in U.S. Pat. Nos. 4,215,064; 4,233,192 and 4,380,637 to Lindemann et al., U.S. Pat. Nos. 4,209,449; 4,336,385 and 4,503,002 to Mayhew et al., and U.S. Pat. Nos. 4,243,602; 4,283,542 and 4,336,386 to O'Lenick et al. These synthetic phospholipids are suggested as exhibiting an outstanding combination of surfactant characteristics as well as being well tolerated by human tissue, i.e., they exhibit exceptionally low ocular irritation and oral toxicity. While these known phospholipids have been found useful as surfactants in a variety of personal care, they have not exhibited an ability to protect the skin from irritation or provide barrier properties to the skin, protecting it from the negative effects of chemicals and environmental effects.

It is very desirable to provide a material from aqueous solution that have a combination of surfactant properties, including foaming, detergency and wetting. The compounds of the present invention provide a wide range of surfactant properties in a single molecule and consequently are referred to as biominimetric-multi-functional surface-active agents. They can be formulated into a plethora of personal care products ranging from baby wipes to body washes and other skin products. In addition the structure of the compounds provides for outstanding substantivity and the phospholipid nature of the molecule allow for very mild natural like materials that can be used in products where low irritation is important.

SUMMARY OF THE INVENTION

Objective of the Invention

It is the objective of the invention to provide a novel phospholipid that contains in the same molecule a phosphated fatty alcohol or fatty alcohol alkoxylate and a process of its use which comprises contacting the hair with an effective surface active concentration of the novel phospholipid. The effective conditioning concentration ranges from between 0.1 and 25% by weight.

In accordance with the present invention we have now been discovered novel phospholipid compound, which conform to the following structure: A phospholipid, which conforms to the following structure;

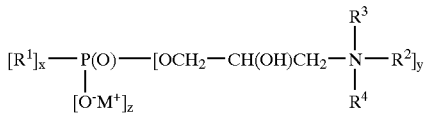

wherein;

$R^1$ is $R^5$—$(OCH_2CH_2O)_a$—$(CH_2CH(CH_3)O)_b$—$(OCH_2CH_2O)_c$— a, b and c are independently integers ranging from 0 to 20;

x, and z are integers independently ranging from 1 to 2;

y is 0 or 1, with the proviso that x+y+z=3;

$R^2$ is selected from the group consisting of;

$CH_3$—$(CH_2)_d$—

$CH_3$—$(CH_2)_e$—$C(O)$—$N(H)$—$(CH_2)_3$—

$CH_3(CH_2)_f CH$=$CH$—$(CH_2)_g$— and $CH_3(CH_2)_h CH$=$CH$—$(CH_2)_i$-$C(O)$—$N(H)$—$(CH_2)_3$—

$R^3$ is selected from the group consisting of —$CH_3$, —$CH_2CH_3$, and —$(CH_2CH_2O)_j$—$(CH_2CH(CH_3)O)_k$—$(OCH_2CH_2O)_m$—$H$ $R^4$ is selected from the group consisting of —$CH_3$, —$CH_2CH_3$, and —$(CH_2CH_2O)_j$—$(CH_2CH(CH_3)O)_k$—$(OCH_2CH_2O)_m$—$H$ $R^5$ is selected from the group consisting of $CH_3$—$(CH_2)_r$—

$CH_3(CH_2)_s CH$=$CH$—$(CH_2)_t$— and $CH_3(CH_2)_u$—$C_6H_5$—$O$— d is an integer ranging from 7 to 21;

e is an integer ranging from 6 to 20;

f and g are independently integers ranging from 2 to 20;

h and i are independently integers ranging from 2 to 20;

j, k and m are independently integers ranging from 0 to 20, with the proviso that j+k+m be greater than or equal to 1;

r is an integer ranging from 6 to 21;

s and t are integers ranging from 2 to 20 u is an integer ranging from 7 to 21.

The invention is also directed to a process for cleaning and conditioning hair, which comprises contacting the hair with an effective conditioning amount of a phospholipid, which conforms to the following structure;

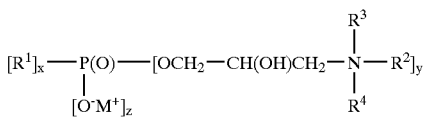

wherein;
 $R^1$ is $R^5$—$(OCH_2CH_2O)_a$—$(CH_2CH(CH_3)O)_b$—$(OCH_2CH_2O)_c$—
 a, b and c are independently integers ranging from 0 to 20;
 x, and z are integers independently ranging from 1 to 2;
 y is 0 or 1, with the proviso that x+y+y=3;
 $R^2$ is selected from the group consisting of;

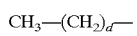

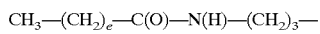

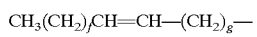

and

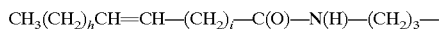

$R^3$ is selected from the group consisting of —$CH_3$, —$CH_2CH_3$, —$(CH_2CH_2O)_j$—$(CH_2CH(CH_3)O)_k$—$(OCH_2CH_2O)_m$—H
 $R^4$ is selected from the group consisting of —$CH_3$, —$CH_2CH_3$, —$(CH_2CH_2O)_n$—$(CH_2CH(CH_3)O)_p$—$(OCH_2CH_2O)_q$—H
 $R^5$ is selected from the group consisting of

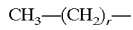

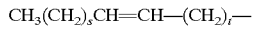

and

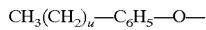

d is an integer ranging from 7 to 21;
 e is an integer ranging from 6 to 20;
 f and g are independently integers ranging from 2 to 20;
 h and i are independently integers ranging from 2 to 20;
 j, k and m are independently integers ranging from 0 to 20, with the proviso that j+k+m be greater than or equal to 1.
 r is an integer ranging from 6 to 21;
 s and t are integers ranging from 2 to 20;
 u is an integer ranging from 7 to 21.

Preferred Embodiments

In a preferred embodiment, $R^2$ is $CH_3$—$(CH_2)_d$—.
In a preferred embodiment, $R^2$ is $CH_3$—$(CH_2)_e$—C(O)—N(H)—$(CH_2)_3$—.
In a preferred embodiment, $R^2$ is $CH_3(CH_2)_f$CH=CH—$(CH_2)_g$—.
In a preferred embodiment, $R^2$ is

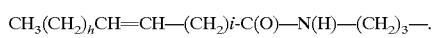

In a preferred embodiment, $R^3$ is —$CH_3$.
In a preferred embodiment, $R^3$ is —$CH_2CH_3$, In a preferred embodiment, $R^3$ is

In a preferred embodiment, $R^4$is —$CH_3$.
In a preferred embodiment, $R^4$is —$CH_2CH_3$.
In a preferred embodiment, $R^4$ is

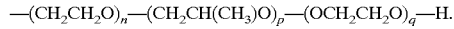

In a preferred embodiment, $R^3$ and $R^4$ are both —$CH_3$
In a preferred embodiment, $R^3$ and $R^4$ are both

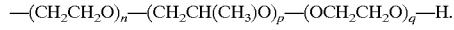

In a preferred embodiment, $R^3$ and $R^4$ are both —$CH_2CH_3$.
In a preferred embodiment the effective conditioning concentration ranges from 0.1 to 25% by weight.

DETAILED DESCRIPTION OF THE INVENTION

The present invention is directed to novel phospholipid compounds, which conform to the following structure: In accordance with the present invention we have now been discovered novel phospholipid compound, which conform to the following structure:

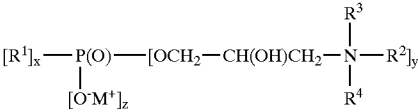

wherein;
 $R^1$ is $R^5$—$(OCH_2CH_2O)_a$—$(CH_2CH(CH_3)O)_b$—$(OCH_2CH_2O)_c$—
 a, b and c are independently integers ranging from 0 to 20;
 x, and z are integers independently ranging from 1 to 2;
 y is 0 or 1, with the proviso that x+y+z=3;
 $R^2$ is selected from the group consisting of;

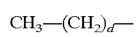

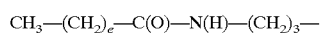

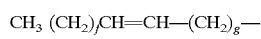

and

$R^3$ is selected from the group consisting of —$CH_3$, —$CH_2CH_3$, and —$(CH_2CH_2O)_j$—$(CH_2CH(CH_3)O)_k$—$(OCH_2CH_2O)_m$—H
 $R^4$ is selected from the group consisting of —$CH_3$, —$CH_2CH_3$, and —$(CH_2CH_2O)_j$—$(CH_2CH(CH_3)O)_k$—$(OCH_2CH_2O)_m$—H
 $R^5$ is selected from the group consisting of

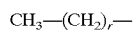

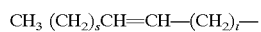

and

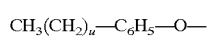

d is an integer ranging from 7 to 21;

e is an integer ranging from 6 to 20;

f and g are independently integers ranging from 2 to 20;

h and i are independently integers ranging from 2 to 20;

j, k and m are independently integers ranging from 0 to 20, with the proviso that j+k+m be greater than or equal to 1;

r is an integer ranging from 6 to 21;

s and t are integers ranging from 2 to 20 u is an integer ranging from 7 to 21.

Phosphate Ester Chemistry

Phosphate esters are part of a class of anionic surface-active agents. The commercial products are complex mixtures including monoester and diester.

The type or types of starting alcohol used determine the functionality of the phosphate ester. Modification of this group is a major factor in the functionality of a phosphate ester.

There are generally two different phosphating agents used commercially. They are polyphosphoric acid (PPA) and phosphorous pentoxide ($P_2O_5$). The selection of phosphating reagent has an effect upon the ratio of the components and upon the functional properties of the resulting phosphate ester.

Reaction

The reaction used to make phosphate esters is referred to as phosphation. It is conducted with either polyphosphoric acid or phosphorus pentoxide and results in a product that is a mixture of mono and diester.

$$R-OH + P_2O_5 \longrightarrow R-O-P(O)-(OH)_2 \quad \text{Monoester}$$

$$(R-O)_2-P(O)-OH \quad \text{Diester}$$

Phosphate esters are marketed at 100% activity in their free acid form or can be neutralized to any desired pH with alkali metals, such as sodium or potassium hydroxide; ammonia and other bases. Additionally, several products are available as partially neutralized forms.

Most phosphate esters are pale yellow to amber, sweet smelling, viscous liquids or pastes, and combine many important properties including (a) stability to extremes of acidity and alkalinity, (b) excellent heat stability (c) high electrolytic tolerance (d) good solubility in alkali, (e) outstanding coupling ability, and (f) outstanding wetting.

Phospholipids

Phospholipids are well known materials and are the topic of a number of patents including U.S. Pat. Nos. 4,215,064; 4,233,192 and 4,380,637 to Lindemann et al., U.S. Pat. Nos. 4,209,449; 4,336,385 and 4,503,002 to Mayhew et al., and U.S. Pat. Nos. 4,243,602; 4,283,542 and 4,336,386 to O'Lenick et al. Until the compounds of the present invention phospholipids were prepared by the reaction of a phosphate salt, like disodium hydrogen phosphate with epichlorohydrin to give a chlorohydroxypropyl intermediate that was subsequently reacted with a tertiary amine to give a phospholipid compound.

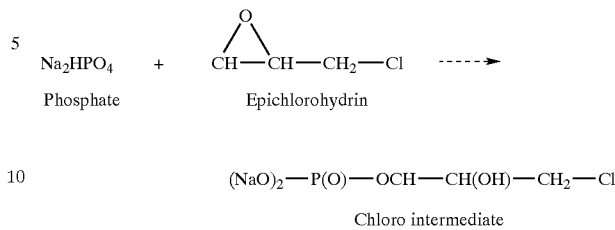

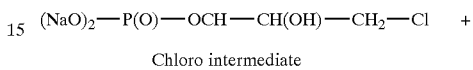

Chloro intermediate

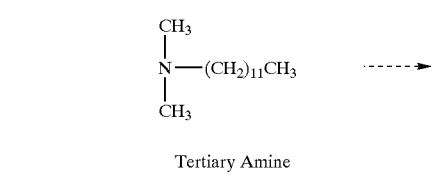

Tertiary Amine

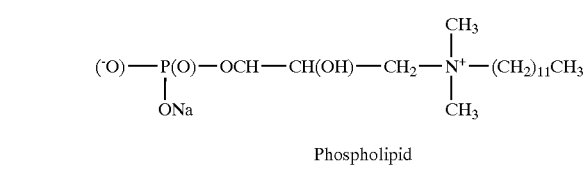

Phospholipid

Phosphate Ester Derived Phospholipids

The products of the present invention use the phosphate esters as the source of the phosphate, thereby incorporating an additional highly functional group into the molecule. It is by the incorporation of this group into the molecule that enhanced surfactant properties are obtained.

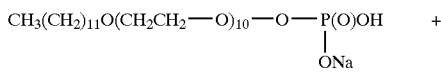

Phosphate Ester Salt

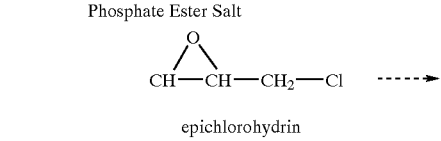

epichlorohydrin

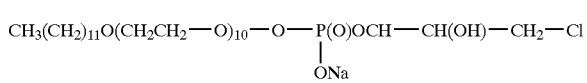

Chloro phosphate ester intermediate

The second reaction is as follows:

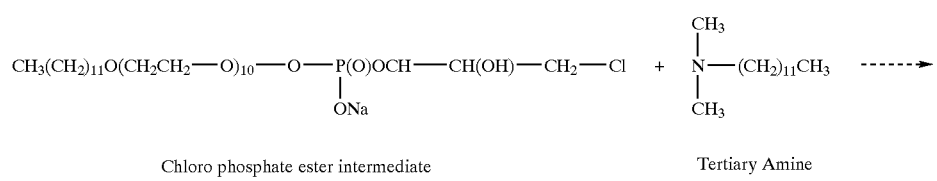

Chloro phosphate ester intermediate                 Tertiary Amine

-continued

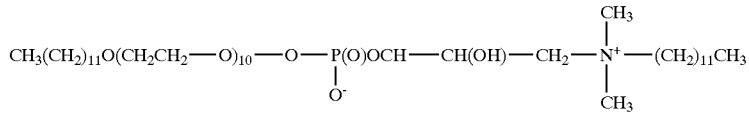

Phosphate Ester Derived Phospholipid

If a diester phosphate is used a compound with no ionizable phosphate group results.

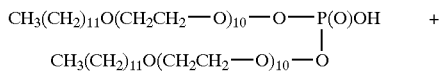

Phosphate Ester Salt

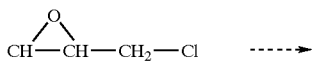

epichlorohydrin

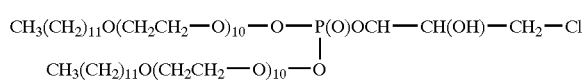

In the diester case, the second reaction is as follows:

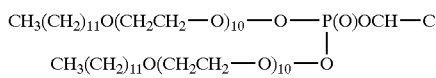 + 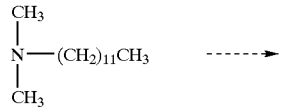 ------>

Chloro phosphate diester intermediate        Tertiary Amine

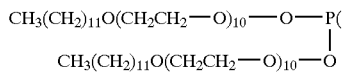 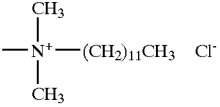 Cl$^-$

Phosphate Di-ester Derived Phospholipid

The resulting product has two phosphate ester groups present and no ionizable phosphate group, resulting in a cationic quaternary compound.

The phosphate monoester compounds are very efficient wetting agents. This attribute makes them very desirable for their ability to wet out fiber like hair and substrates like skin to give uniform deposition of the phospholipid.

The phosphate diester product is an outstanding oil emulsifier. This attribute makes the molecule a better detergent and cleaning agent. The improved detergency makes these compounds more desirable and more functional than the phospholipids made from sodium phosphate.

The fact that the compounds of the present invention are made from phosphate esters, which are commonly mixtures of mono and diester, results in a multifunctional product that provides wide range of properties in the formulation. The mixed products are a preferred embodiment of the invention, truly giving a multi-functional surfactant. Phosphate esters made with polyphosphoric acid result in products having 90%+ monoester. Products made with $P_2O_5$ typically result in products having roughly equal amounts of mono and diester. The resulting phospholipids made from phosphate esters are unique products, due in part to the raw materials used to make them.

EXAMPLES

Phosphate Esters

Phosphate Esters useful in the preparation of the compounds of the present invention are commercially available from a variety of sources including Siltech Corporation, Toronto Ontario Canada.

$R^1$—P(O)—(OH)$_2$ Monoester $(R^1)_2$—P(O)—OH Diester $R^1$ is $R^5$—$(OCH_2CH_2O)_a$—$(CH_2CH(CH_3)O)_b$—$(OCH_2CH_2O)_c$— a, b and c are independently integers ranging from 0 to 20.

Alkyl Phosphate Esters

Compounds of this class are commercially available from a variety of manufacturers including Siltech Corporation of Toronto Ontario Canada. They conform to the following structure;

$[CH_3$—$(CH_2)_r$—$(OCH_2CH_2O)_a$—$(CH_2CH(CH_3)O)_b$—$(OCH_2CH_2O)_c$—$]_x$—P(O)—$[OH]_z$ wherein r is an integer ranging from 6 to 21;

a, b and c are independently integers ranging from 0 to 20.

Products made with polyphosphoric acid are on average 90% monoester, 10% diester. This means on average the "x" value is 0.9 and the average z value is 2.1 to equal three substituents.

| Example | a value | b value | c value | r value | x value | z value | monoester |
|---|---|---|---|---|---|---|---|
| 1 | 0 | 0 | 0 | 6 | 0.9 | 2.1 | 90% |
| 2 | 0 | 0 | 0 | 7 | 0.9 | 2.1 | 90% |

-continued

| Example | a value | b value | c value | r value | x value | z value | monoester |
|---|---|---|---|---|---|---|---|
| 3 | 0 | 1 | 1 | 9 | 0.9 | 2.1 | 90% |
| 4 | 5 | 5 | 5 | 13 | 0.9 | 2.1 | 90% |
| 5 | 0 | 2 | 0 | 15 | 0.9 | 2.1 | 90% |
| 6 | 5 | 1 | 3 | 17 | 0.9 | 2.1 | 90% |
| 7 | 10 | 10 | 5 | 19 | 0.9 | 2.1 | 90% |
| 8 | 20 | 20 | 20 | 21 | 0.9 | 2.1 | 90% |

Products made with $P_2O_5$ are on average 50% monoester, 50% diester. This means on average the "x" value is 1.5 and the average z value is 1.5 to equal three substituents.

| Example | a value | b value | c value | r value | x value | z value | monoester |
|---|---|---|---|---|---|---|---|
| 9 | 0 | 0 | 0 | 6 | 1.5 | 1.5 | 50% |
| 10 | 0 | 2 | 5 | 7 | 1.5 | 1.5 | 50% |
| 11 | 10 | 10 | 10 | 9 | 1.5 | 1.5 | 50% |
| 12 | 20 | 20 | 20 | 13 | 1.5 | 1.5 | 50% |
| 13 | 2 | 2 | 2 | 15 | 1.5 | 1.5 | 50% |
| 14 | 5 | 2 | 10 | 17 | 1.5 | 1.5 | 50% |
| 15 | 10 | 5 | 3 | 19 | 1.5 | 1.5 | 50% |
| 16 | 10 | 1 | 5 | 21 | 1.5 | 1.5 | 50% |

Alkylene Phosphate Esters

Compounds of this class are commercially available from a variety of manufacturers including Siltech Corporation of Toronto Ontario Canada. They conform to the following structure;

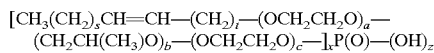

wherein s and t are integers ranging from 2 to 20;

The unsaturated alcohols of interest for the preparation of the compounds of the current invention include;

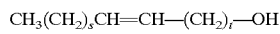

| Designation | Name | Formula | s | t |
|---|---|---|---|---|
| C12:1 | Lauroleyl alcohol | $C_{12}H_{22}O$ | 2 | 8 |
| C14:1 | Myristoleyl alcohol | $C_{14}H_{26}O$ | 4 | 8 |
| C16:1 | Palmitoleyl alcohol | $C_{16}H_{30}O$ | 5 | 8 |
| C18:1 | Oleyl alcohol | $C_{18}H_{34}O$ | 8 | 8 |
| C20:1 | Gadoleyl alcohol | $C_{20}H_{38}O$ | 10 | 8 |
| C22:1 | Erucyl alcohol | $C_{22}H_{42}O$ | 10 | 10 |

Products made with polyphosphoric acid are on average 90% monoester, 10% diester. This means on average the "x" value is 0.9 and the average z value is 2.1 to equal three substituents.

| Example | a Value | b Value | c value | s value | t value | x value | z value | monoester |
|---|---|---|---|---|---|---|---|---|
| 17 | 0 | 0 | 0 | 2 | 8 | 0.9 | 2.1 | 90% |
| 18 | 5 | 5 | 5 | 4 | 8 | 0.9 | 2.1 | 90% |
| 19 | 0 | 0 | 10 | 5 | 8 | 0.9 | 2.1 | 90% |
| 20 | 20 | 20 | 20 | 8 | 8 | 0.9 | 2.1 | 90% |
| 21 | 5 | 2 | 10 | 10 | 8 | 0.9 | 2.1 | 90% |
| 22 | 10 | 5 | 5 | 10 | 10 | 0.9 | 2.1 | 90% |

Products made with $P_2O_5$ are on average 50% monoester, 50% diester. This means on average the "x" value is 1.5 and the average z value is 1.5 to equal three substituents.

| Example | a Value | b Value | c value | s value | t value | x value | z value | monoester |
|---|---|---|---|---|---|---|---|---|
| 23 | 0 | 0 | 0 | 2 | 8 | 1.5 | 1.5 | 50% |
| 24 | 5 | 5 | 5 | 4 | 8 | 1.5 | 1.5 | 50% |
| 25 | 0 | 0 | 10 | 5 | 8 | 1.5 | 1.5 | 50% |
| 26 | 20 | 20 | 20 | 8 | 8 | 1.5 | 1.5 | 50% |
| 27 | 5 | 2 | 10 | 10 | 8 | 1.5 | 1.5 | 50% |
| 28 | 10 | 5 | 5 | 10 | 10 | 1.5 | 1.5 | 50% |

Alkyl Aryl Phosphate Esters

Compounds of this class are commercially available from a variety of manufacturers including Siltech Corporation of Toronto Ontario Canada. They conform to the following structure;

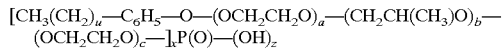

wherein u is an integer ranging from 7 to 21.

Products made with polyphosphoric acid are on average 90% monoester, 10% diester. This means on average the "x" value is 0.9 and the average z value is 2.1 to equal three substituents.

| Example | a value | b value | c value | u value | x value | z value | monoester |
|---|---|---|---|---|---|---|---|
| 29 | 0 | 0 | 0 | 7 | 0.9 | 2.1 | 90% |
| 30 | 5 | 1 | 15 | 19 | 0.9 | 2.1 | 90% |
| 31 | 20 | 5 | 10 | 21 | 0.9 | 2.1 | 90% |

Products made with $P_2O_5$ are on average 50% monoester, 50% diester. This means on average the "x" value is 1.5 and the average z value is 1.5 to equal three substituents.

| Example | a value | b value | c value | u value | x value | z value | monoester |
|---|---|---|---|---|---|---|---|
| 32 | 0 | 0 | 0 | 7 | 1.5 | 1.5 | 50% |
| 31 | 20 | 5 | 10 | 21 | 1.5 | 1.5 | 50% |

Preparation of 3-chloro-2-hydroxypropyl Phosphate Ester Intermediate

General Reaction

To a suitable reaction vessel equipped with reflux condenser, thermometer and agitation is added the specified number of grams of the specified phosphate ester (examples 1 to 33), the specified number of grams of water, under good agitation. The pH is then adjusted with the specified 45% aqueous base to a pH of 7.5. Mix well until a solution is obtained. Next add 141.0 grams of Epichlorohydrin under agitation. Apply heat to 90 C., refluxing back into the vessel any distillate. As the temperature increases to 95–100 C. the contents will clear. Hold at this temperature for 3–4 hours. The resulting product is a 40% aqueous solution of;

|  | Phosphate Ester |  | Water | Base |
|---|---|---|---|---|
| Example | Example | Grams | Grams | Type |
| 34 | 1 | 179.0 | 642.0 | NaOH |
| 35 | 2 | 184.0 | 650.0 | KOH |
| 36 | 3 | 315.0 | 912.0 | NaOH |
| 37 | 4 | 1003.0 | 2288.0 | NaOH |
| 38 | 5 | 397.0 | 976.0 | KOH |
| 39 | 6 | 735.0 | 1752.0 | NaOH |
| 40 | 7 | 1612.0 | 3504.0 | KOH |
| 41 | 8 | 2268.0 | 4818.0 | NaOH |
| 42 | 9 | 171.5 | 625.0 | NaOH |
| 43 | 10 | 786.0 | 1854.0 | NaOH |
| 44 | 11 | 2459.0 | 5200.0 | KOH |
| 45 | 12 | 3575.0 | 7432.0 | NaOH |
| 46 | 13 | 821.0 | 1924.0 | NaOH |
| 47 | 14 | 1606.0 | 3494.0 | KOH |
| 48 | 15 | 1780.0 | 3842.0 | KOH |
| 49 | 16 | 985.0 | 2252.2 | NaOH |
| 50 | 17 | 288.0 | 738.0 | NaOH |
| 51 | 18 | 1129.0 | 2540.0 | KOH |
| 52 | 19 | 1108.0 | 2500.0 | KOH |
| 53 | 20 | 3614.0 | 7510.0 | NaOH |
| 54 | 21 | 1267.0 | 2816.0 | NaOH |
| 55 | 22 | 1492.0 | 3266.0 | KOH |
| 56 | 23 | 432.0 | 1152.0 | KOH |
| 57 | 24 | 1693.0 | 3668.0 | NaOH |
| 58 | 25 | 1662.0 | 3606.0 | KOH |
| 59 | 26 | 5421.0 | 11124.0 | NaOH |
| 60 | 27 | 1900.0 | 4082.0 | KOH |
| 61 | 28 | 2238.0 | 4758.0 | NaOH |
| 62 | 29 | 316.0 | 914.0 | NaOH |
| 63 | 30 | 1533.0 | 3348.0 | KOH |
| 64 | 31 | 2083.0 | 4448.0 | NaOH |
| 65 | 32 | 430.0 | 1142.0 | NaOH |
| 66 | 33 | 2841.0 | 5964.0 | KOH |

Tertiary Amines

There are a wide number of tertiary amines that can be used in the preparation of the compounds of the present invention. All are commercially available.

Alkyl Tertiary Amines

This class of compounds is available from a variety of commercial sources, including Kao Chemical, High Point N.C. They conform to the following structure:

$$CH_3-(CH_2)_d-N-(CH_3)_2$$

wherein d is an integer ranging from 7 to 21;

| Example | d Value |
|---|---|
| 67 | 7 |
| 68 | 9 |
| 69 | 11 |
| 70 | 13 |
| 71 | 15 |
| 72 | 17 |
| 73 | 19 |
| 74 | 21 |

Alkylene Tertiary Amines

This class of compounds is available from a variety of commercial sources, including Kao Chemical, High Point N.C. They conform to the following struture:

$$CH_3(CH_2)_fCH=CH-(CH_2)_g-N-(CH_3)_2$$

wherein f and g are independently integers ranging from 2 to 20.

| Example | f value | g value |
|---|---|---|
| 75 | 2 | 8 |
| 76 | 4 | 8 |
| 77 | 5 | 8 |
| 78 | 8 | 8 |
| 79 | 10 | 8 |
| 80 | 10 | 10 |

Alkyl Amido Tertiary Amines

This class of compounds is available from a variety of commercial sources, including Siltech Corporation Toronto Ontario Canada. They conform to the following structure:

$$CH_3-(CH_2)_e-C(O)-N(H)-(CH_2)_3-N-(CH_3)_2$$

wherein e is an integer ranging from 6 to 20;

| Example | e Value |
|---|---|
| 81 | 6 |
| 82 | 8 |
| 83 | 10 |
| 84 | 12 |
| 85 | 14 |
| 86 | 18 |
| 87 | 20 |

Alkyl Amido Alkylene Tertiary Amines

This class of compounds is available from a variety of commercial sources, including Siltech Corporation Toronto Ontario Canada. They conform to the following struture:

$$CH_3(CH_2)_hCH=CH-(CH_2)_i-C(O)-N(H)-(CH_2)_3-$$

wherein h and i are independently integers ranging from 2 to 20.

| Example | h Value | i Value |
|---|---|---|
| 88 | 2 | 7 |
| 89 | 4 | 7 |
| 90 | 5 | 7 |
| 91 | 8 | 7 |
| 92 | 10 | 7 |
| 93 | 10 | 9 |

Alkoxy Alkyl Tertiary Amines

This class of compounds is available from a variety of commercial sources, including Siltech Corporation Toronto Ontario Canada. They conform to the following structure:

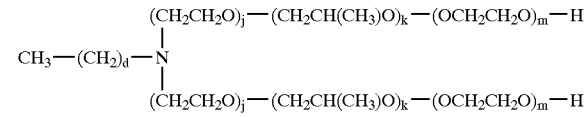

wherein d is an integer ranging from 7 to 21 and j, k and m are independently integers ranging from 0 to 20, with the proviso that j+k+m be greater than or equal to 1.

| Example | d value | i value | k value | m value |
|---------|---------|---------|---------|---------|
| 94 | 7 | 1 | 0 | 0 |
| 95 | 11 | 2 | 1 | 5 |
| 96 | 16 | 0 | 10 | 10 |
| 97 | 19 | 20 | 20 | 20 |
| 98 | 21 | 10 | 2 | 10 |

Preparation of the Phospholipid of the Present Invention

Into a suitable reaction flask is charged the specified number of grams of de-ionized water and the various 3-chloro-2-hydroxypropyl phosphate ester intermediates (Examples 34–66) is next added into the reaction vessel. Heat is applied to 90.degree. C. Next, the specified number of grams of the specified tertiary amine (examples 67–98 ) are charged into the reaction vessel under good agitation. The temperature is maintained at between 90.degree. C. and 95.degree. C., until the percentage of free tertiary amine is 0.5% maximum. During the reaction time the pH is kept at between 7 and 8 with NaOH as required, The reaction mass will clear when the product is at 90 C. for about 1 hour. The reaction time is approximately 6 to 9 hours. The % NaCl is monitored and the reaction is deemed complete when the % of theoretical NaCl reaches 98%.

| | Chloro Phosphate | Water | Tertiary amine | |
|---------|---------|-------|---------|-------|
| Example | Example | Grams | Example | Grams |
| 99 | 34 | 314.0 | 67 | 157.0 |
| 100 | 35 | 370.0 | 68 | 185.0 |
| 101 | 36 | 426.0 | 69 | 213.0 |
| 102 | 37 | 482.0 | 70 | 241.0 |
| 103 | 38 | 536.0 | 71 | 268.0 |
| 104 | 39 | 594.0 | 72 | 297.0 |
| 105 | 40 | 650.0 | 73 | 325.0 |
| 106 | 41 | 706.0 | 74 | 353.0 |
| 107 | 42 | 422.0 | 75 | 211.0 |
| 108 | 43 | 476.0 | 76 | 238.0 |
| 109 | 44 | 504.0 | 77 | 252.0 |
| 110 | 45 | 608.0 | 78 | 304.0 |
| 111 | 46 | 644.0 | 79 | 322.0 |
| 112 | 47 | 700.0 | 80 | 350.0 |
| 113 | 48 | 426.0 | 81 | 213.0 |
| 114 | 49 | 510.0 | 82 | 255.0 |
| 115 | 50 | 538.0 | 83 | 269.0 |
| 116 | 51 | 594.0 | 84 | 297.0 |
| 117 | 52 | 650.0 | 85 | 325.0 |
| 118 | 53 | 762.0 | 86 | 381.0 |
| 119 | 54 | 818.0 | 87 | 409.0 |
| 120 | 55 | 510.0 | 88 | 255.0 |
| 121 | 56 | 566.0 | 89 | 283.0 |
| 122 | 57 | 594.0 | 90 | 297.0 |
| 123 | 58 | 678.0 | 91 | 339.0 |
| 124 | 59 | 734.0 | 92 | 367.0 |
| 125 | 60 | 790.0 | 93 | 395.0 |
| 126 | 61 | 430.0 | 94 | 215.0 |
| 127 | 62 | 1854.0 | 95 | 927.0 |
| 128 | 63 | 916.0 | 96 | 459.0 |
| 129 | 64 | 12350.0 | 97 | 6175.0 |
| 130 | 65 | 4638.0 | 98 | 2319.0 |

APPLICATIONS EXAMPLES

The compounds above examples 99–130 are aqueous solutions of the phospholipids of the current invention. They are used without additional purification.

The compounds are multi functional surfactants. That is they exhibit wetting properties, foam properties and are subatantive to hair and skin. They provide good cleansing properties and are very mild to skin and eyes.

These products can be used in personal care applications, like shampoos, bubble bath products, body wash and as a wetting agent and detergent for use in wipes designed for babies.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A process for cleaning and conditioning hair which comprises contacting the hair with an effective conditioning amount of a phospholipid, which conforms to the following structure;

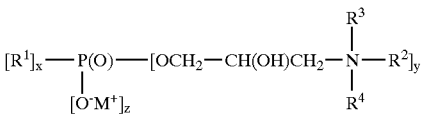

wherein;

$R^1$ is $R^5$—$(OCH_2CH_2O)_a$—$(CH_2CH(CH_3)O)_b$—$(OCH_2CH_2O)_c$— a, b and c are independently integers ranging from 0 to 20;

x, and z are integers independently ranging from 1 to 2;

y is 0 or 1, with the proviso that x+y+y=3;

$R_2$ is selected from the group consisting of;

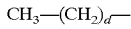

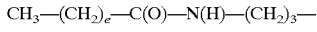

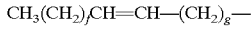

and

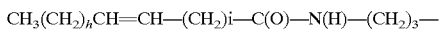

$R^3$ is selected from the group consisting of —$CH_3$, —$CH_2CH_3$, —$(CH_2CH_2O)_j$—$(CH_2CH(CH_3)O)_k$—$(OCH_2CH_2O)_m$—H $R^4$ is selected from the group consisting of —$CH_3$, —$CH_2CH_3$, —$(CH_2CH_2O)_n$—$(CH_2CH(CH_3)O)_p$—$(OCH_2CH_2O)_q$—H $R^5$ is selected from the group consisting of

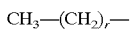

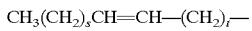

and

d is an integer ranging from 7 to 21;

e is an integer ranging from 6 to 20;

f and g are independently integers ranging from 2 to 20;

h and i are independently integers ranging from 2 to 20;

j, k and m are independently integers ranging from 0 to 20, with the proviso that j+k+m be greater than or equal to 1 r is an integer ranging from 6 to 21;

s and t are integers ranging from 2 to 20;

u is an integer ranging from 7 to 21.

2. A process of claim 1 wherein said effective conditioning concentration ranges from 0.1 to 25% by weight.

3. A process of claim 2 wherein $R^2$ is $CH_3—(CH_2)_d—$.

4. A process of claim 2 wherein $R^2$ is $CH_3—(CH_2)_e—C(O)—N(H)—(CH_2)_3—$.

5. A process of claim 2 wherein $R^2$ is $CH_3(CH_2)_f CH=CH—(CH_2)_g—$.

6. A process of claim 1 wherein $R^2$ is

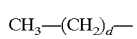

7. A phospholipid, which conforms to the following structure;

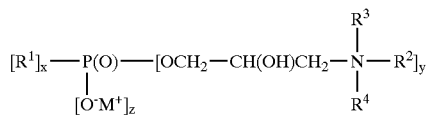

wherein;

$R^1$ is $R^5 —(OCH_2CH_2O)_a—(CH_2CH(CH_3)O)_b—(OCH_2CH_2O)_c—$ a, b and c are independently integers ranging from 0 to 20;

x, and z are integers independently ranging from 1 to 2;

y is 0 or 1, with the proviso that x+y+y=3;

$R^2$ is selected from the group consisting of;

$CH_3—(CH_2)_d—$ $CH_3—(CH_2)_e—C(O)—N(H)—(CH_2)_3—$ $CH_3(CH_2)_f CH=CH—(CH_2)_g—$ and $CH_3(CH_2)_h CH=CH—(CH_2)_i—C(O)—N(H)—(CH_2)_3—$ $R^3$ is selected from the group consisting of $—CH_3$, $—CH_2CH_3$, $—(CH_2CH_2O)_j—(CH_2CH(CH_3)O)_k—(OCH_2CH_2O)_m—H$ $R^4$ is selected from the group consisting of $—CH_3$, $—CH_2CH_3$, 13 $(CH_2CH_2O)_n—(CH_2CH(CH_3)O)_p—(OCH_2CH_2O)_q—H$ $R^5$ is selected from the group consisting of $CH_3—(CH_2)_r—$ $CH_3(CH_2)_s CH=CH—(CH_2)_t—$ and $CH_3(CH_2)_u—C_6H_5—O—$ d is an integer ranging from 7 to 21;

e is an integer ranging from 6 to 20;

f and g are independently integers ranging from 2 to 20;

h and i are independently integers ranging from 2 to 20;

j, k and m are independently integers ranging from 0 to 20, with the proviso that j+k+m be greater than or equal to 1 r is an integer ranging from 6 to 21;

s and t are integers ranging from 2 to 20;

u is an integer ranging from 7 to 21.

8. A phospholipid of claim 1 wherein $R^2$ is $CH_3—(CH_2)_d—$.

9. A phospholipid of claim 1 wherein $R^2$ is $CH_3—(CH_2)_e—C(O)—N(H)—(CH_2)_3—$.

10. A phospholipid of claim 1 wherein $R^2$ is $CH_3 (CH_2)_f CH=CH—(CH_2)_g—$.

11. A phospholipid of claim 1 wherein $R^2$ is

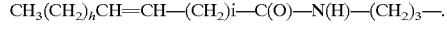

12. A phospholipid of claim 1 wherein $R^3$ is $—CH_3$.

13. A phospholipid of claim 1 wherein $R^3$ is $—CH_2CH_3$.

14. A phospholipid of claim 1 wherein $R^3$ is $—(CH_2CH_2O)_j—(CH_2CH(CH_3)O)_k—(OCH_2CH_2O)_m—H$.

15. A phospholipid of claim 1 wherein $R^4$ is $—CH_3$.

16. A phospholipid of claim 1 wherein $R^4$ is $—CH_2CH_3$.

17. A phospholipid of claim 1 wherein $R^4$ is $—(CH_2CH_2O)_n—(CH_2CH(CH_3)O)_p—(OCH_2CH_2O)_q—H$.

18. A phospholipid of claim 1 wherein $R^3$ and $R^4$ are both $—CH_3$.

19. A phospholipid of claim 1 wherein $R^3$ and $R^4$ are both $—(CH_2CH_2O)_n—(CH_2CH(CH_3)O)_p—(OCH_2CH_2O)_q—H$.

20. A phospholipid of claim 1 wherein $R^3$ and $R^4$ are both $—CH_2CH_3$.

* * * * *